(12) United States Patent
Kasinrerk

(10) Patent No.: US 9,285,367 B2
(45) Date of Patent: Mar. 15, 2016

(54) THREE-COLOR REAGENT FOR MEASUREMENT OF CD4 POSITIVE LYMPHOCYTES BY FLOW CYTOMETRY

(75) Inventor: Watchara Kasinrerk, Amphur Muang (TH)

(73) Assignees: National Science and Technology Development Agency (TH); The Thailand Research Fund (TH)

(*) Notice: Subject to any disclaimer, the term of this patent is extended or adjusted under 35 U.S.C. 154(b) by 1215 days.

(21) Appl. No.: 10/461,544

(22) Filed: Jun. 16, 2003

(65) Prior Publication Data

US 2004/0110122 A1    Jun. 10, 2004

(51) Int. Cl.
   *G01N 33/533*    (2006.01)
   *G01N 33/569*    (2006.01)

(52) U.S. Cl.
   CPC ........ *G01N 33/56972* (2013.01); *G01N 33/533* (2013.01); *G01N 2333/70514* (2013.01)

(58) Field of Classification Search
   CPC .......... G01N 33/56972; G01N 33/533; G01N 2333/70514
   USPC .............. 435/2, 7.2, 7.24, 40.5, 343.1, 343.2, 435/344, 374, 973; 436/548, 10, 63, 64
   See application file for complete search history.

(56) References Cited

U.S. PATENT DOCUMENTS 6,998,476 B2 * 2/2006 Strom et al. ................. 536/23.5

OTHER PUBLICATIONS

Gerstner et al., Immunophenotyping of peripheral blood lymphocytes by laser scanning cytometry, Journal of Immunological Methods 246 (1-2): 175-185 (Dec. 1, 2000).*
Kasinrerk et al., Production of monoclonal antibody to CD4 antigen and development of reagent for CD4+ lymphocyte enumeration (Journal of the Medical Association of Thailand 81(11): 879-892 (Nov. 1998) Abstract.*
Greimers et al., Cubic: A Three Dimensional Colored Projection of Consort 30 Generated Trivariate Flow Cytometric Data, Cytometry 12: 570-575 (1991).*
Schmid et al. Measurement of lymphocyte subset proliferation by three-color immunofluorescence and DNA flow cytometry. Journal of Immunological Methods 235: 121-131 (2000).*
Carbonari et al. A Unified Procedure for Conservative (Morphology) and Integral (DNA and Immunophenotype) Cell Staining for Flow Cytometry. Cytometry 4 (2): 120-125 (Jun. 2001).*

* cited by examiner

*Primary Examiner* — Gail R Gabel
(74) *Attorney, Agent, or Firm* — Nuttina Netsuwan

(57) ABSTRACT

The developed reagent is three-color immunophenotyping reagent for measurement of CD4 positive lymphocytes in peripheral blood. The reagent contains 7-aminoactinomycin D (7-AAD) which intercalates into double stranded DNA and is easily excited at 488 nm. The fluorescence emission of 7-AAD has peak at 670 nm that can be detected with FL3 detector of flow cytometer. The 7-AAD, therefore, stains white blood cells and discriminates it from red blood cells. The reagent also contains fluorescein isothiocyanate (FITC) labeled CD4 monoclonal antibody and phycoerythrin (PE) labeled CD14 monoclonal antibody which are detected with FL1 and FL2 detectors of flow cytometer, respectively. The developed reagent can be used to measure number of CD4 positive lymphocytes in lymphocyte population and monitor monocyte contamination simultaneously. This reagent therefore provides more accuracy results of CD4 positive lymphocyte enumeration.

2 Claims, 4 Drawing Sheets

By FL1 and FL2 monitoring, cells in the acquisition lymphocyte gate obtained from sample tube are set for distinguishing fluorescence-negative and positive cell populations.

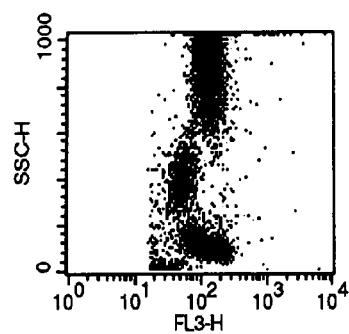
Figure 1. By FL3 and SSC acquisition, the FL3 threshold is adjusted to gate out red blood cells from the 7-AAD stained white blood cells which having bright red fluorescence.

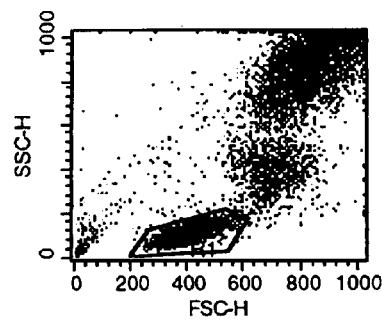
Figure 2. By FSC and SSC monitoring, lymphocyte population is gated according to their size and granularity.

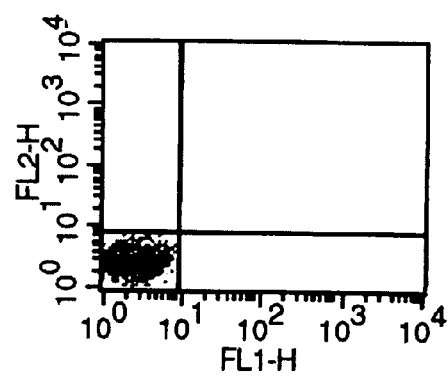
Figure 3. By FL1 and FL2 monitoring, cells in the acquisition lymphocyte gate obtained from the control tube are set as fluorescence-negative cell populations

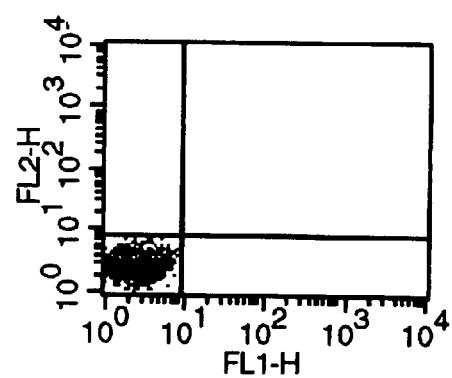
Figure 4. By FL1 and FL2 monitoring, cells in the acquisition lymphocyte gate obtained from sample tube are set for distinguishing fluorescence-negative and positive cell populations.

THREE-COLOR REAGENT FOR MEASUREMENT OF CD4 POSITIVE LYMPHOCYTES BY FLOW CYTOMETRY

CROSS-REFERENCE TO RELATED APPLICATION

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Human immunodeficiency virus (HIV) is a retrovirus that infects cells those possess the CD4 receptor. This infection causes the depletion of CD4 positive lymphocytes, which is a major clinical finding in progressive infection. In HIV infection, the absolute number of CD4 positive lymphocytes is an important marker for prognosis, classification of the state of disease, treatment decision and monitoring of therapy. Immunophenotyping using lysed whole blood stained with monoclonal antibody panels and analyzed by flow cytometry is the current standard method for determination of CD4 positive lymphocytes.

Recently several types of immunophenotyping reagents for measurement of CD4 positive lymphocytes have been developed and routinely used in clinical laboratory. The three-color immunophenotyping reagent is a common flow cytometric reagent for determining CD4 positive lymphocytes in routine laboratory. The available three-color reagents contain peridinin chlorophyll protein (PerCP) or phycoerythrincyanin 5.1 (PE-Cy5) labeled CD45 monoclonal antibody for discrimination of white blood cells (leucocytes) and red blood cells (erythrocytes) and contain FITC labeled CD3 monoclonal antibody and PE labeled CD4 monoclonal antibody for enumeration of CD4 positive lymphocytes. Unlike two-color reagent, a disadvantage of three-color reagents is that it cannot indicate number of monocytes that are contaminated in the lymphocyte population gated during flow cytometric measurement. If significant numbers of the contaminated monocytes are presented in the acquisition lymphocyte gate, the obtained CD4 positive lymphocyte number will be erroneously decreased.

We have developed a three-color reagent that can enumerate percentage of CD4 positive lymphocytes in lymphocyte population and can determine the contamination of monocytes in the acquisition lymphocyte gate, simultaneously. This reagent contains 7-aminoactinomycin D (7-AAD) which can intercalate into double stranded DNA of white blood cells and allow white blood cells, but not red blood cells, to be detected with FL3 detector of flow cytometer. The reagent also contains FITC labeled CD4 monoclonal antibody and PE labeled CD14 monoclonal antibody, which allow CD4 positive cells and monocytes to be detected with FL1 and FL2 detector, respectively.

BRIEF SUMMARY OF THE INVENTION

The developed reagent is a three-color immunophenotyping reagent for measurement of CD4 positive lymphocytes in peripheral blood by flow cytometry. The reagent contains 7-aminoactinomycin D (7-AAD) which intercalates into double stranded DNA. The fluorescence emission of 7-AAD has peak at 670 nm that can be detected with FL3 detector of flow cytometer. The 7-AAD, therefore, stains white blood cells and discriminates it from red blood cells. The reagent also contains fluorescein isothiocyanate (FITC) labeled CD4 monoclonal antibody and phycoerythrin (PE) labeled CD14 monoclonal antibody which can be detected with FL1 and FL2 detectors of flow cytometer, respectively. The developed reagent can be used to measure number of CD4 positive lymphocytes in lymphocyte population and monitor monocyte contamination in the acquisition lymphocyte population, simultaneously. This reagent therefore provides more accuracy results of CD4 positive lymphocyte measurement.

BRIEF DESCRIPTION OF THE SEVERAL VIEWS OF THE DRAWING(S)

FIG. 1. By FL3 and SSC acquisition, the FL3 threshold is adjusted to gate out red blood cells from the 7-AAD stained white blood cells which having bright red fluorescence.

FIG. 2. By FSC and SSC monitoring, lymphocyte population is gated according to their size and granularity.

FIG. 3. By FL1 and FL2 monitoring, cells in the acquisition lymphocyte gate obtained from the control tube are set as fluorescence-negative cell populations FIG. 4. By FL1 and FL2 monitoring, cells in the acquisition lymphocyte gate obtained from sample tube are set for distinguishing fluorescence-negative and positive cell populations.

DETAILED DESCRIPTION OF THE INVENTION

1. Production of Hybridomas Producing CD4 and CD14 Monoclonal Antibodies

For CD4 monoclonal antibody production, Balb/C mouse was immunized with SupT1 cell line. For CD14 monoclonal antibody production, Balb/C mouse was immunized with CD14 expressing COS cells. By using standard hybridoma technique, hydridoma producing CD4 monoclonal antibody (named MT4) and hybridoma producing CD14 monoclonal antibody (named MT14/3) were generated. MT4 and MT14/3 monoclonal antibodies are IgM and IgG1 isotype, respectively. The MT4 and MT14/3 hybridoma cells of the invention were deposited, in accordance with The Budapest Treaty of 1977 at the Leibniz Institute DSMZ-German Collection of Microorganisms and Cell Cultures located at Inhoffenstr. 7B D-38124 Braunschweig, Germany. The MT4 hybridoma cells of the invention were deposited under Accession Number DSM ACC3178 and the MT14/3 hybridoma cells of the invention were deposited under Accession Number DSM ACC3185.

2. Production of FITC Labeled CD4 Monoclonal Antibody and PE-Labeled CD14 Monoclonal Antibody Ascitic fluids containing CD4 and CD14 monoclonal antibody were obtained by inoculating of MT4 and MT14/3 hybridoma clones into Balb/C mice. CD4 and CD14 monoclonal antibodies were purified from ascites by affinity chromatography using anti-mouse IgM coated sepharose column and protein G coated sepharose column, respectively. Purified CD4 monoclonal antibodies were conjugated with FITC and purified CD14 monoclonal antibodies were conjugated with PE.

3. Immunofluorescence Staining

Ten microliters of 7-AAD solution, FITC labeled CD4 monoclonal antibody and PE labeled CD14 monoclonal antibody are added into 100 µl of EDTA-whole blood in 12×75 mm tube (sample tube). For control, only 10 µl of 7-AAD solution is added into 100 µl of blood in 12×75 mm tube (control tube). All tubes are gently mixed and incubated at room temperature for 30 minutes in the dark. Following the incubation period, 2 ml of RBC lysing solution is added and incubated for another 10 minutes. After centrifugation at 500×g for 5 minutes and subsequent washed with 2 ml PBS containing 0.1% sodium azide, the cell pellets are resuspended in 0.5 ml of 1% paraformaldehyde in PBS. The stained cells are then analyzed by a flow cytometer.

4. Flow Cytometric Analysis

4.1 Flow Cytometer Setting

The control tube is used firstly to set up the flow cytometer. By acquisition using FL3 and SSC, red blood cells are gated out from the 7-AAD stained white blood cells having bright red fluorescence by the FL3 threshold (FIG. 1). The remained white blood cells are analyzed using FSC/SSC and lymphocyte population is gated according to their size and granularity (FIG. 2). By monitoring of FL1 and FL2, cells in the gated lymphocyte population are set as fluorescence-negative cell populations (FIG. 3).

Then, tube containing cells stained with FITC labeled CD4 and PE labeled CD14 monoclonal antibodies is used to set up the flow cytometer. The red blood cells are removed and the lymphocyte population is gated as described above. By FL1 and FL2 detector, cells in the acquisition lymphocyte gate are used to set marker for distinguishing fluorescence-negative and positive cell populations (FIG. 4).

4.2 Enumeration of CD4 Positive Lymphocytes

The minimum of 10,000 cells is measured for both control and sample tubes. By monitoring of FL3 and SSC, red blood cells are gated out from the 7-AAD stained white blood cells by the FL3 threshold. The remained white blood cells are analyzed using FSC/SSC and lymphocyte population is gated according to their size and granularity. By FL1 and FL2, cells in gated lymphocyte population in the control tube are used to determine non-specific binding and set marker for distinguishing fluorescence-negative and positive cell populations. The percentages of CD4 positive lymphocytes in gated lymphocyte population are determined from the sample tube by using FL1 and FL2. By this measurement, the CD4 positive lymphocytes are CD14−/CD4+ population. While the CD14+ population indicates the number of monocytes that contaminated in the gated lymphocyte population.

5. Composition of the Developed Reagent 1. 7-aminoactinomycin D (7-AAD) concentration of 100 µg/ml in phosphate buffer saline (PBS) pH 7.2
2. FITC labeled CD4 monoclonal antibody and PE labeled CD14 monoclonal antibody

SEQUENCE LISTING

Not Applicable

I claim:

1. A reagent for measurement of CD4 positive lymphocytes in whole blood using flow cytometry, the reagent consisting essentially of:
   a) 7-aminoactinomycin D (7-AAD) configured to discriminate between erythrocytes and leucocytes;
   b) CD4 monoclonal antibody conjugated to a fluorescent label; and,
   c) CD14 monoclonal antibody conjugated to a fluorescent label;
   wherein the CD4 monoclonal antibody is produced by MT4 hybridoma clone of which is deposited with the DSMZ under Accession Number DSM ACC3178 and the CD14 monoclonal antibody is produced by MT14/3 hybridoma clone of which is deposited with the DSMZ under Accession Number DSM ACC3185;
   wherein the CD4 monoclonal antibody and the CD14 monoclonal antibody are differentially labeled using fluorescein isothiocyanate (FITC) and phycoerythrin (PE); and,
   wherein the reagent is configured to simultaneously detect and enumerate CD4 positive lymphocytes in a lymphocyte population while reducing contamination of monocytes present in the whole blood sample using flow cytometric analysis.

2. A kit for measurement of CD4 positive lymphocytes in whole blood using flow cytometry, the kit consisting essentially of:
   a) 7-AAD configured to discriminate between erythrocytes and leucocytes;
   b) CD4 monoclonal antibody conjugated to a fluorescent label; and,
   c) CD14 monoclonal antibody conjugated to a fluorescent label;
   wherein the CD4 monoclonal antibody is produced by MT4 hybridoma clone of which is deposited with the DSMZ under Accession Number DSM ACC3178 and the CD14 monoclonal antibody is produced by MT14/3 hybridoma clone of which is deposited with the DSMZ under Accession Number DSM ACC3185;
   wherein the CD4 monoclonal antibody and the CD14 monoclonal antibody are differentially labeled using fluorescein isothiocyanate (FITC) and phycoerythrin (PE); and,
   wherein the kit is configured to simultaneously detect and enumerate CD4 positive lymphocytes in a lymphocyte population while reducing contamination of monocytes present in the whole blood sample using flow cytometric analysis.

* * * * *